United States Patent [19]
Kaiser et al.

[11] Patent Number: 5,423,813
[45] Date of Patent: Jun. 13, 1995

[54] RESECTOSCOPE AND ELECTRODE ASSEMBLY

[75] Inventors: Mark S. Kaiser, New Haven; Clifford F. Potocky, Shelton, both of Conn.

[73] Assignee: Coopersurgical, Shelton, Conn.

[21] Appl. No.: 33,541

[22] Filed: Mar. 18, 1993

[51] Int. Cl.⁶ .............................................. A61B 17/39
[52] U.S. Cl. ............................................................ 606/46
[58] Field of Search ........................ 128/639, 642, 4, 6, 128/7; 606/45, 46, 129, 170, 47, 48

[56] References Cited

U.S. PATENT DOCUMENTS

| | | |
|---|---|---|
| 538,971 | 5/1895 | Laughlin . |
| 712,989 | 11/1902 | Washburn . |
| 1,930,214 | 10/1933 | Wappler . |
| 2,120,598 | 3/1937 | Beuoy . |
| 3,149,633 | 6/1961 | Zingale . |
| 3,752,159 | 8/1973 | Wappler . |
| 3,850,175 | 11/1974 | Iglesias . |
| 3,856,015 | 12/1974 | Iglesias . |
| 3,898,991 | 8/1975 | Ikuno et al. . |
| 3,901,242 | 8/1975 | Storz . |
| 3,910,279 | 10/1975 | Okada et al. . |
| 3,939,839 | 2/1976 | Curtiss . |
| 3,942,530 | 3/1976 | Northeved . |
| 3,973,568 | 8/1976 | Iglesias . |
| 3,990,456 | 11/1976 | Iglesias . |
| 4,024,869 | 5/1977 | Bonnet . |
| 4,030,502 | 6/1977 | Iglesias . |
| 4,060,087 | 11/1977 | Hiltebrandt et al. . |
| 4,068,667 | 1/1978 | Iglesias . |
| 4,116,198 | 9/1978 | Roos . |
| 4,132,227 | 1/1979 | Ibe . |
| 4,134,406 | 1/1979 | Iglesias . |
| 4,149,538 | 4/1979 | Mrava et al. . |
| 4,181,131 | 1/1980 | Ogin . |
| 4,362,160 | 12/1982 | Hiltebrandt . |
| 4,423,727 | 1/1984 | Widran et al. ................. 606/46 |
| 4,430,996 | 2/1984 | Bonnet . |
| 4,481,948 | 11/1984 | Sole . |
| 4,506,668 | 3/1985 | Konig . |
| 4,538,610 | 9/1985 | Kubota . |
| 4,552,146 | 11/1985 | Jensen et al. . |
| 4,569,133 | 2/1986 | Schmidt . |
| 4,625,713 | 12/1986 | Hiraoka . |
| 4,648,399 | 3/1987 | Nakada . |
| 4,649,917 | 3/1987 | Karasawa . |
| 4,657,018 | 11/1987 | Hakky . |
| 4,674,503 | 6/1987 | Peyman et al. . |
| 4,726,370 | 2/1988 | Karasawa et al. . |
| 4,744,361 | 5/1988 | Karasawa . |
| 4,750,489 | 6/1988 | Berkman et al. . |
| 4,776,336 | 10/1988 | Karasawa . |
| 4,834,095 | 5/1989 | Miller . |
| 4,917,082 | 4/1990 | Grossi et al. . |
| 4,917,621 | 4/1990 | Grossi . |
| 4,919,131 | 4/1990 | Grossi et al. . |
| 4,955,884 | 9/1990 | Grossi . |
| 5,112,329 | 5/1992 | Storz ................................ 606/46 |

FOREIGN PATENT DOCUMENTS

684198 6/1930 France .

Primary Examiner—Lee S. Cohen
Assistant Examiner—Brian M. Green
Attorney, Agent, or Firm—Vorys, Sater, Seymour & Pease

[57] ABSTRACT

The present invention relates to an improved resectoscope which enhances versatile and ergonomic operating and handling performance thereof. The resectoscope includes a plurality of thumb engageable portion's a central block assembly used to displace an electrode from a sheath of the resectoscope. Also disclosed is a drip guard assembly which coacts with the outer sheath and is releasably retained in any one of a plurality of positions on the outer sheath so as to accommodate different operations and patients. Additionally, provision is made for improved electrode guiding and stabilizing structures which enhance stability of the electrode assembly by facilitating easy and correct insertion of the electrode without requiring disassembly of resectoscope components.

7 Claims, 11 Drawing Sheets

RESECTOSCOPE AND ELECTRODE ASSEMBLY

BACKGROUND OF THE INVENTION

The present invention is directed generally to the field of resectoscopes and, more particularly, to an improved resectoscope assemblage for providing versatile and ergonomic operating and handling performances.

Resectoscopes are typically used for removing tissue from the prostrate gland. Generally, resectoscopes include a hollow sheath which is insertable into an urethra. The sheath surrounds both a telescopic tube assembly so that a procedurist may view the operation and an operating resecting electrode assembly. The electrode assembly is connected at its proximal end to a manually operable working member. A procedurist's hand applies a force against the working member. This is done by placing a thumb through a single thumb ring and pressing against it in order to overcome a biasing means being applied against the working member, thereby urging an electrode tip from the sheath to a resecting or operating mode. After resection, the electrode tip is withdrawn into the sheath by the procedurist's release of the biasing force coupled to the working member. One such type of resectoscope is described in U.S. Pat. No. 3,990,456 issued to J. Iglesias. This type provides generally satisfactory operation. However, there is a continuing desire to improve upon its overall reliability as well as ease of operability. For instance, one drawback typically associated with it is that some procedurists do not always feel comfortable advancing the electrode. Discomfort tends to arise because the procedurist's thumb is required to be in a fixed relationship to the resectoscope. Considering that these operations last for relatively long periods of time, for instance up to one hour, the repeated withdrawals tend to become uncomfortable and inconvenient for the user. Another disadvantage, is that manufacturers have positioned the thumb ring on a fixed or dedicated part of the resectoscope. Since the rectoscope is used in multiple positions during the procedures, a fixed ring position does not always allow for user comfort or manipulation ease of obtaining accessible operating positions.

Still another shortcoming associated with known resectoscopes is that the process of changing electrodes during procedures requires relatively time consuming disassembly and assembly of the sheath and other components. This obviously results in a major inconvenience.

Also, known resectoscopes use drip shields which have fixed relationships to the outer sheath and this fact limits generally the versatility of the resectoscope in terms of dealing not only with different patients, but for performing different types of operations.

Also, still other known resectoscopes are often difficult to assemble and disassemble for maintenance problems because the number of parts associated therewith.

Accordingly, there is a continuing desire to improve upon known resectoscopes.

SUMMARY OF THE INVENTION

In accordance with the present invention, provision is made for an improved resectoscope which enhances versatile and ergonomic operating and handling performances thereof. Included in the improved resectoscope is a biased electrode positioning means. This is actuated by a procedurist's thumb applying a force against a biasing force provided by biasing means of the positioning means in order to displace the positioning means and thereby urge an electrode means connected to it from an outer sheath of the resectoscope to a resecting condition at a surgical site.

In an illustrated embodiment, the electrode positioning means includes means for defining a plurality of thumb engageable portions which are conveniently arranged so that a procedurist's thumb can easily engage anyone of the thumb engageable portions during the course of a procedure.

In another illustrated embodiment, the electrode positioning means includes a central block assembly coupled to a proximal end portion of the electrode means and has a plurality of projections extending generally laterally and inferiorly to an axis generally parallel to a longitudinal axis of the resectoscope's outer sheath assembly.

In another illustrated embodiment, there is included a drip guard assembly which adjustably coacts with the outer sheath and is releaseably retained in anyone of a plurality of positions on the outer sheath so as to accommodate performance of different operations and different patients.

In another illustrated embodiment, provision is made for improved electrode guiding and stabilizing structures which enhance stability of the electrode assembly during use and easy replacement of the electrode assembly by facilitating easy and correct insertion of the electrode without requiring disassembly of several rectoscope components.

Accordingly, among the objects which are provided by the present invention are the following: an improved resectoscope which enhances the ease of operation and versatility thereof; an improved resectoscope in which it is easy to replace the electrode assembly and provide enhanced electrode stability; an improved resectoscope with an improved biased electrode positioning device; an improved resectoscope in which the biased electrode positioning means includes means for permitting positioning of a procedurists' thumb at a plurality of spaced positions; an improved resectoscope of the lasted noted type in which the outer sheath assembly need not be disassembled for replacement of the electrode assembly; an improved resectoscope which is manufactured in an inexpensive yet reliable manner; an improved resectoscope having an improved assembly for detachably retaining a drip shield to anyone of a plurality of positions along an outer sheath thereof; an improved resectoscope having improved structure for guiding and stabilizing the electrode; and, an improved resectoscope which is ergonomically constructed for versatile, comfortable and prolonged use.

Other objects and the full scope of the present invention will become apparent upon review of the detailed description to follow when taken in conjunction with the accompanying drawings in which like parts are designated by like reference numerals throughout the several views.

DETAILED DESCRIPTION

Reference is made to FIGS. 1-11 for illustrating preferred embodiment of an improved resectoscope 10 made according to the principles of the present invention. Basically, the improved resectoscope 10 includes an outer sheath assembly 12, telescopic assembly 14, electrode positioning assembly 16, and electrode assembly 18.

Initial reference is made to the telescopic assembly 14 at the proximal or viewing end of the resectoscope 10. The telescopic assembly 14 permits a procedurist to view the operation. Included in the telescopic assembly 14 is a rod lens system 20 having located at a proximal end thereof a suitable eyepiece 22 and a lightsource assembly 24 which is operable for providing illumination during performance of an operation. The telescopic assembly 14 includes a telescopic tube 20 made of stainless steel which carries the optics. The tube 20 extends into the outer sheath assembly 12 as well as through the electrode positioning assembly 16 in a manner which is conventional. The telescopic assembly 14 includes a scope locking collar assembly 26 including a scope locking collar pin 28 that is operable to removably secure the telescopic tube 20 to the collar 26. A spring guide rod 30 is secured at one end to a backstop 31 of the locking collar assembly 26 and at the other end to the front stop 38. A telescopic guide tube 32 is connected to the locking collar assembly 26 at one end, as shown best in FIG. 4, and cooperates as by being spot welded at the other end with the irrigation tube 70. The guide tube 32 provides a housing for the scope tube 20. The telescopic assembly 14 preferred for use can be a Hysteroscope 30° Assembly available from CooperSurgical. Of course, other types of scopes can be used.

Figure 1:
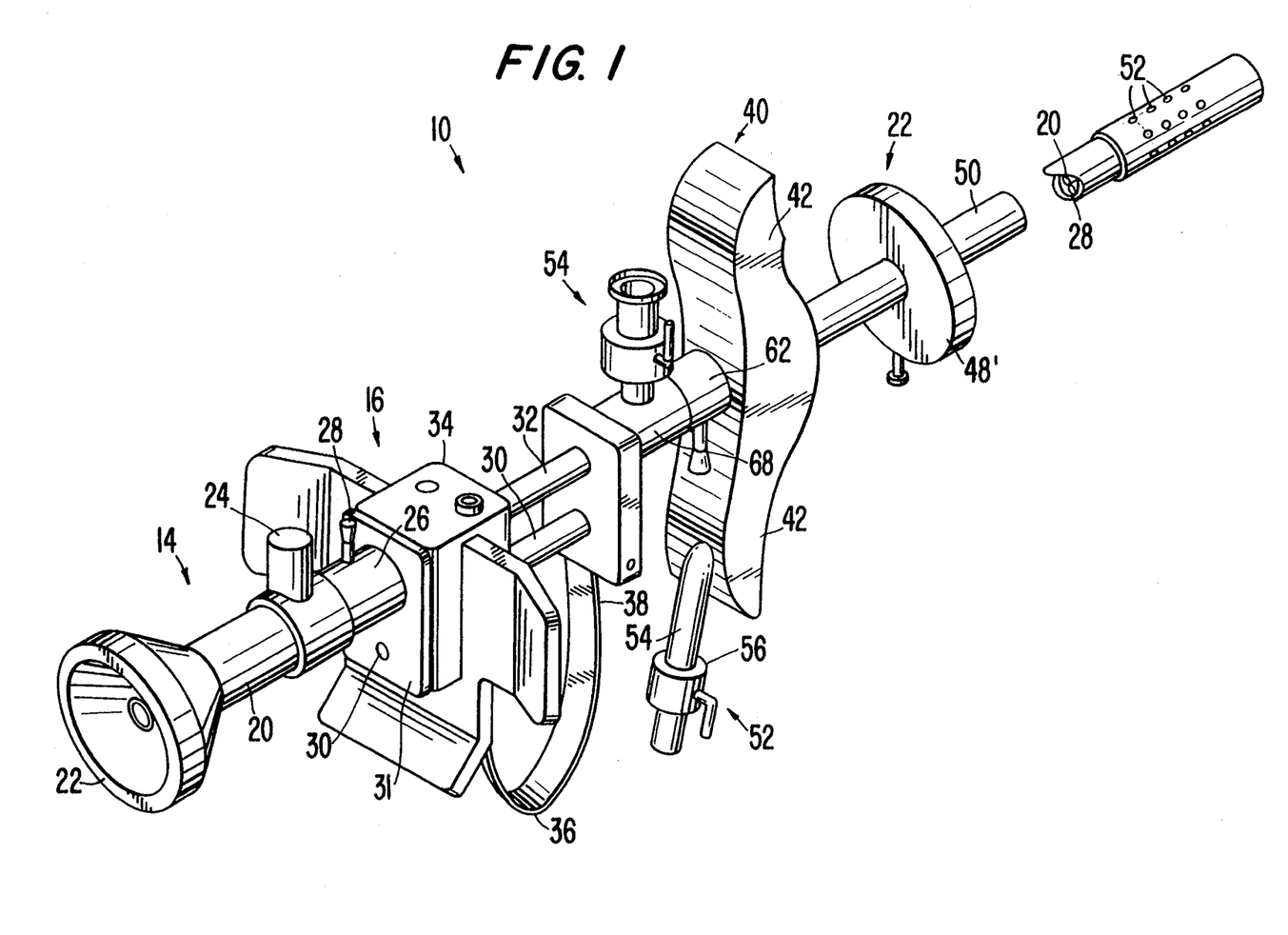
FIG. 1 is a perspective view of one improved resectoscope embodiment made in accordance with the principles of the present invention, but with an improved adjustable grip guard assembly associated therewith.
Figure 2:
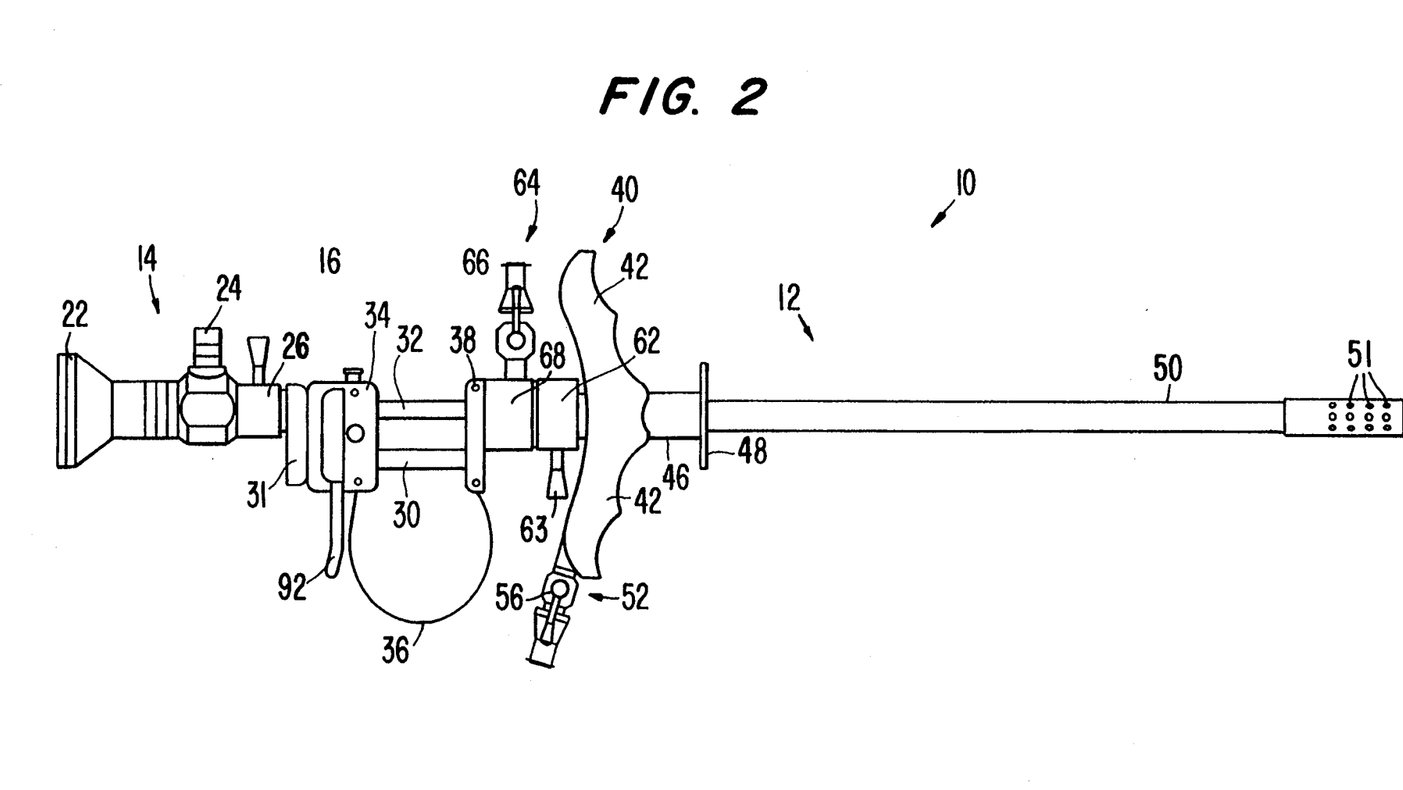
FIG. 2 is an elevational view of a resectoscope depicted in FIG. 1.
Figure 4:
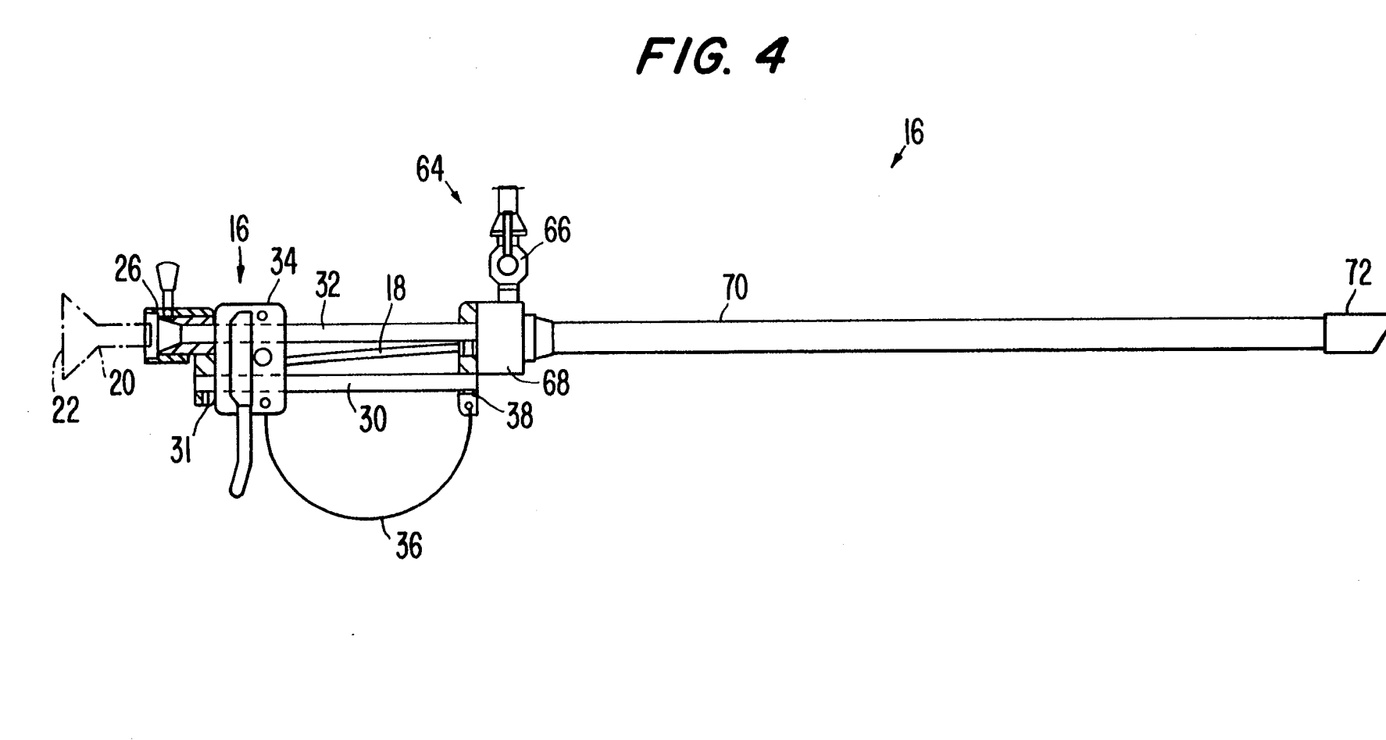
FIG. 4 is an elevational view, partly in cross-section, of an irrigation tube and working element assembly.

Reference is made to FIGS. 1, 2, 4, 8 and 9 for illustrating the electrode positioning assembly 16. The electrode positioning assembly 16 is mounted on the telescopic guide tube 32 and the spring guide rod 30 for reciprocal movement relative thereto between a non-resecting position, and a resecting position; as will be described hereinafter. The electrode positioning assembly 16 is seen to comprise a central block or working member assembly 34 and a flat bowed compression spring 36 which has one of its terminal end portions affixed to the central block assembly 34 and its other end to the front stop 38 (FIGS. 2 and 4). The compression spring 36 functions to urge the central block assembly 34 against the backstop 31 and forces a tip of the electrode assembly 18 to its withdrawn or non-resecting condition within the insulation tip 72. The spring 36 provides a biasing resistance which the procedurist must overcome when effecting operation of the resectoscope 10 so as to drive the electrode assembly 18 to its resecting or extended position (not shown). The spring rate of the spring 36 be selected so that it gradually forces the central block assembly 34 to the position depicted in FIGS. 1, 2 and 4.

Figure 3:
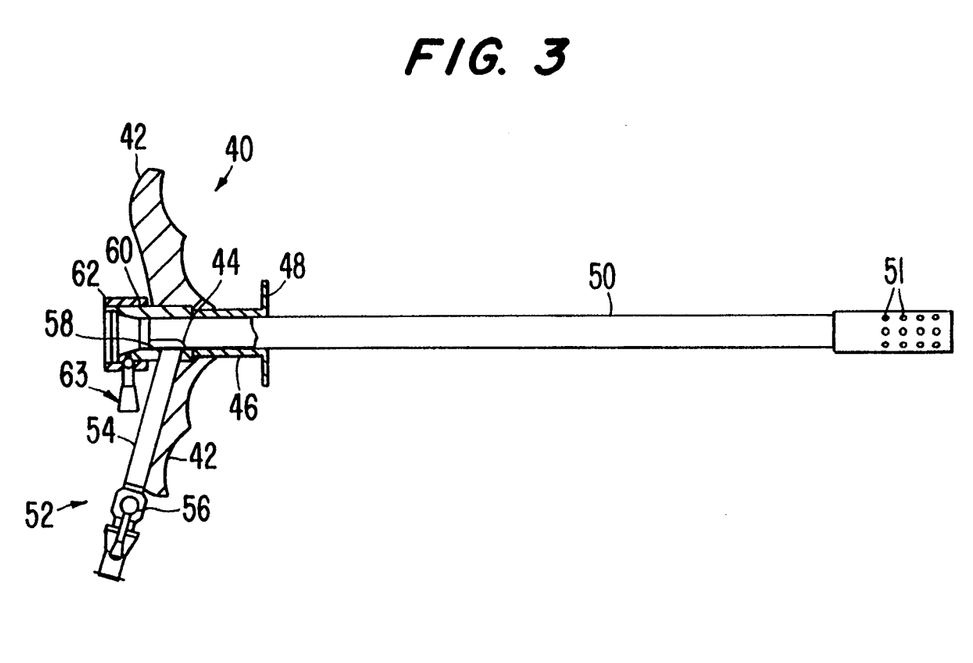
FIG. 3 is a elevational view, partly in cross-section, of an outer sheath assembly.

Reference is made now to FIGS. 1-3 for better illustrating the outer sheath assembly 12 which has secured thereto an interlock 68 attached to front stop 38. The stop member 38 also allows the guide tube 32 to extend through it. It will be seen that one end of the compression spring 36 is also secured to the front stop member 38 and the electrode positioning member 16 is adapted to abut against the front stop member 38 so as to inhibit forward movement thereof and thereby define the extent the electrode assembly extends from it.

As best seen in FIGS. 1-3, a handle assembly 40 is connected to the outer sheath assembly 12 and includes diametrically opposed and generally vertical finger grip surfaces 42 on a finger grip. As seen in FIG. 3, the finger grip surfaces 42 define an annular recess 44 for receiving a sleeve segment 46 of a drip ring or shield 48 that is affixed appropriately to a tubular elongated outer sheath 50. The present invention also envisions an adjustable drip shield 48' as seen in FIG. 1 which is selectively positionable along the length of the outer sheath 50 so that different operations and patients can be easily accommodated. The outer sheath 50 is made of an appropriate stainless steel member that is sized for effecting the type of operation desired (e.g. urological, gynecological). In one application this embodiment, the sheath 50 is dimensioned for use in effecting uterus operations and thus is adapted to be inserted in the cervix. In addition, the outer sheath can be provided with a plurality of circumferential rows of aspiration openings 51 which are sized to aspirate the vaporized tissue, etc. by having the apertures arranged circumferential (e.g. 360°) is that they permit a procedurist to rotate the sheath relative to the patient for effecting different types of operations (e.g., urological and gynecological) without suffering a diminishment of the aspirating functions.

Extending through the lower finger grip element 44 is an aspiration tube assembly 52. The aspiration tube assembly includes an aspiration tube 54 that is connectable at one end through a stop cock 56 to a source of negative pressure or gravity (not shown). At another end, the aspirating tube 54 terminates at an opening 58 in a female sheath interlock member 60 which is connected to the outer sheath 50. A locking collar 62 having a collar pin 63 is connected to the interlock 60.

Aspiration is performed in a conventional manner. In this regard, the stop cock 56 is operated so as to allow a procedurist to control the flow rate of aspiration.

Figure 5:
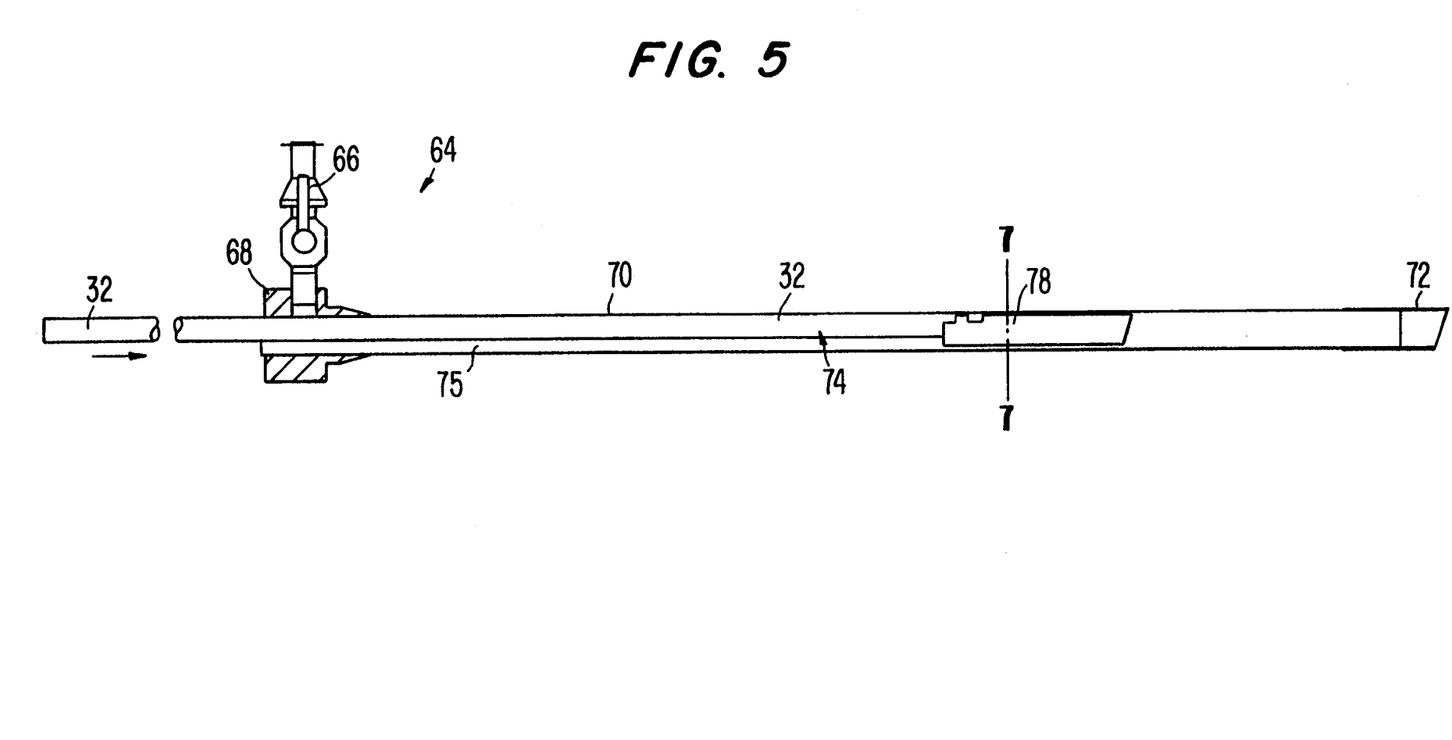
FIG. 5 is a cross-sectional view of the irrigation tube assembly depicting an improved guide and stabilizing assembly.

Reference is now made to FIGS. 4 and 5 for illustrating an irrigation tube assembly 64. Included in the tube assembly 64 is an inlet stop cock 66 assembly that is fluidly coupled to a male sheath interlock 68. The interlock 68 is selectively coupled to the female interlock 60 by the locking collar 62. The stop cock 66 allows regulation of the flow of irrigation fluid from a suitable source (not shown) to the surgical site. In this regard there is attached to the male interlock 68 an irrigation tube 70 which is disposed within the outer sheath or tube 50 for carrying the irrigating fluid to the operative site. The irrigation tube 70 is provided with an insulation tip 72.

Figure 6:
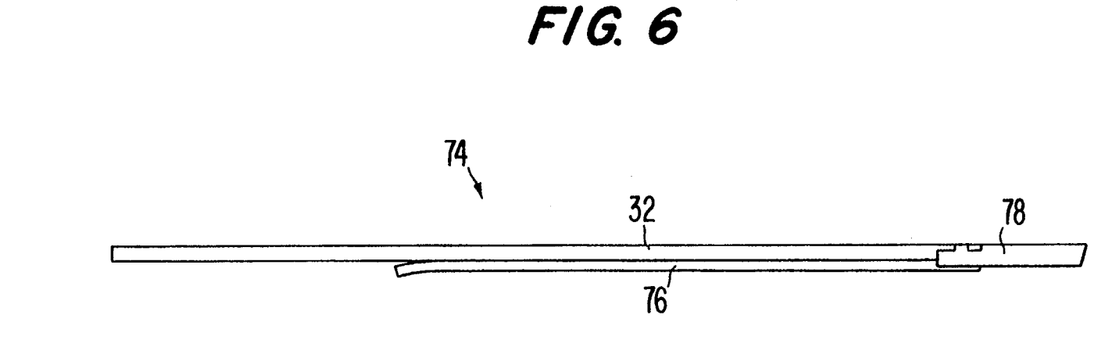
FIG. 6 is an elevational view of a telescopic and electrode guide assembly made according to the present invention.
Figure 7:
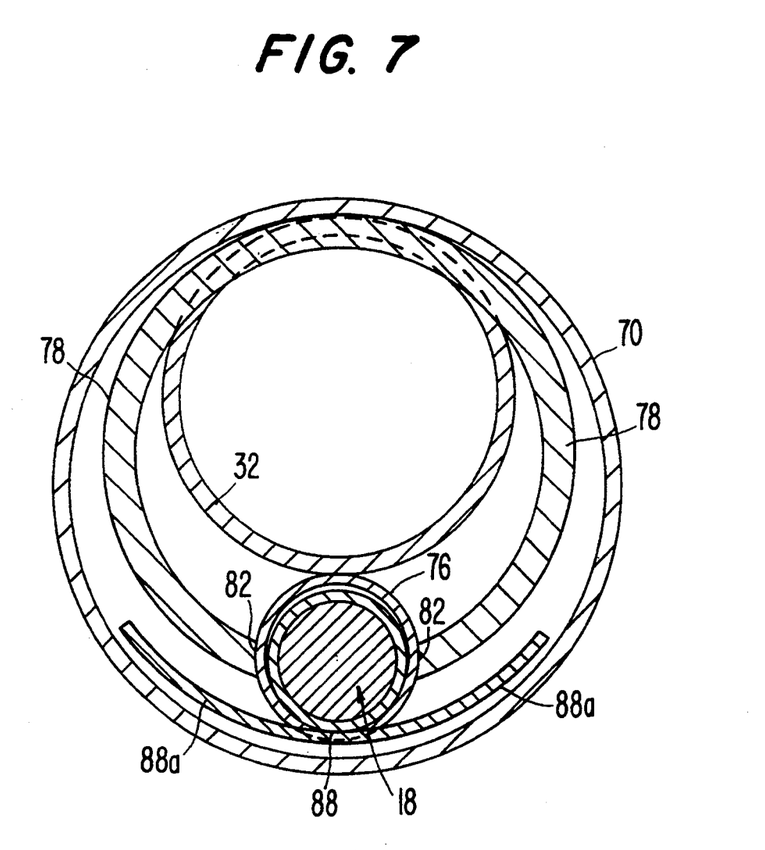
FIG. 7 is a cross-sectional view taken along section line 7—7 appearing in FIG. 5 including an electrode and wing assembly.
Figure 8:
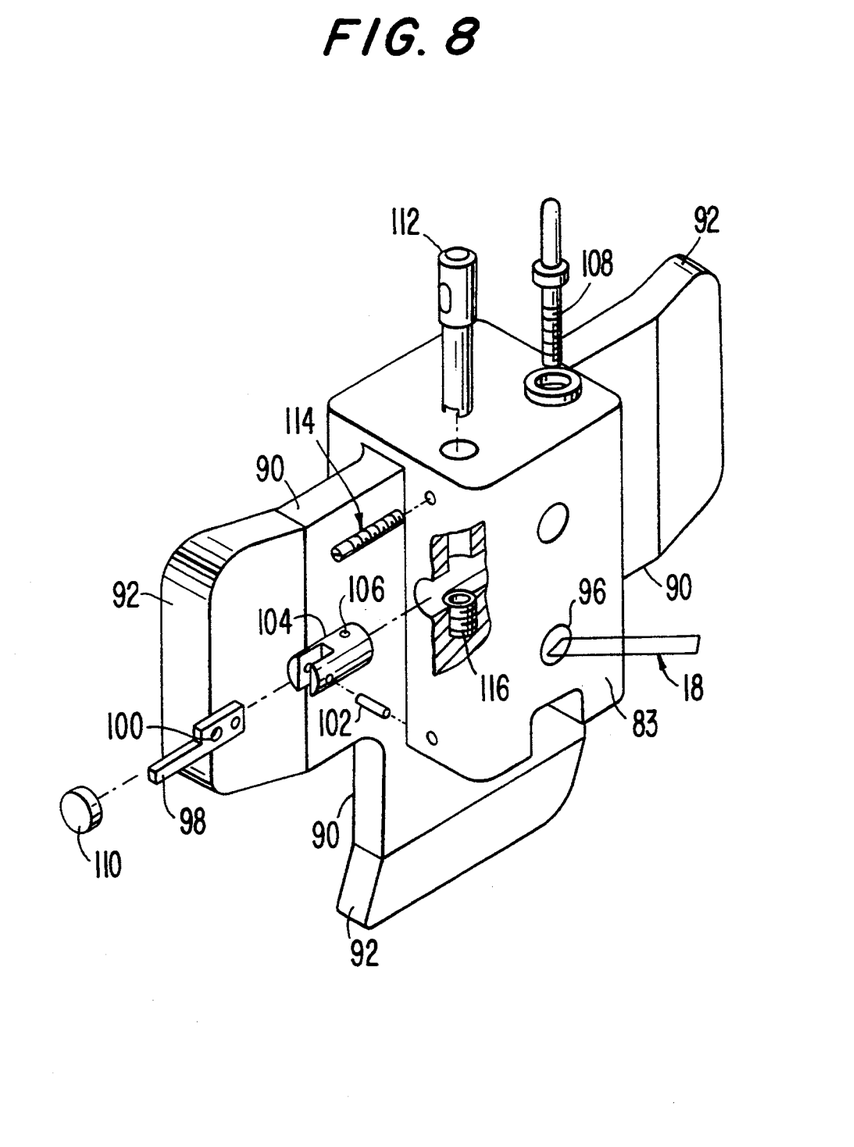
FIG. 8 is a front perspective view of a working member made according to the principles of the present invention.
Figure 9:
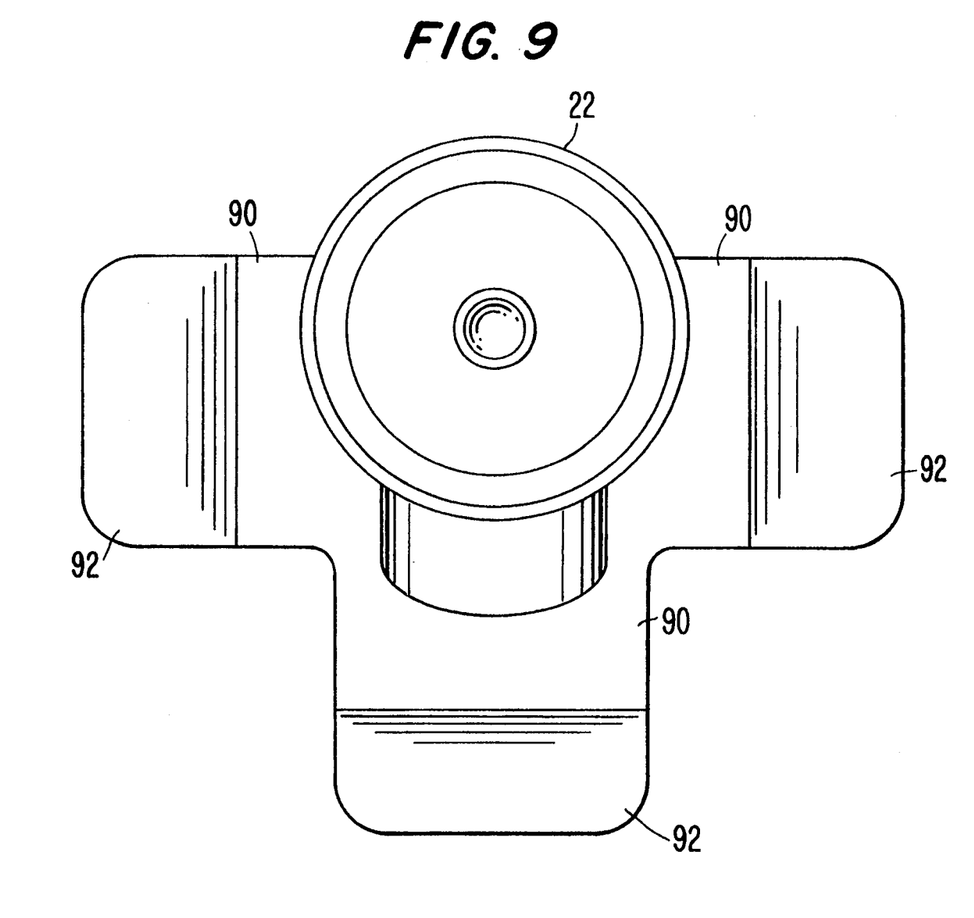
FIG. 9 is an end view of the resectoscope with portions omitted but illustrating the telescopic eyepiece and the improved electrode positioning assembly of the present invention.
Figure 10A:
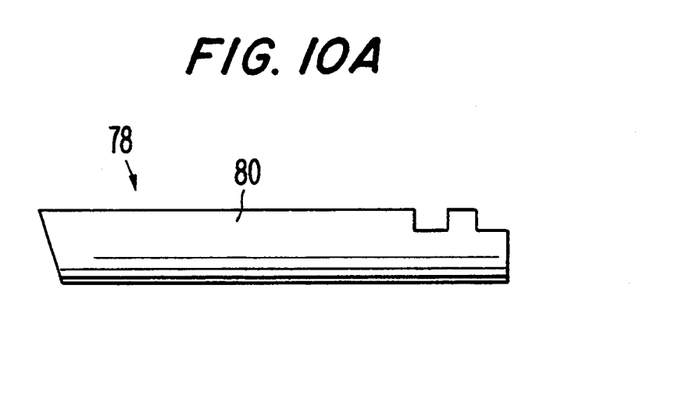
FIGS. 10a and 10b illustrate elevational and bottom views; respectively, of a guide made according to the present invention.
Figure 10B:
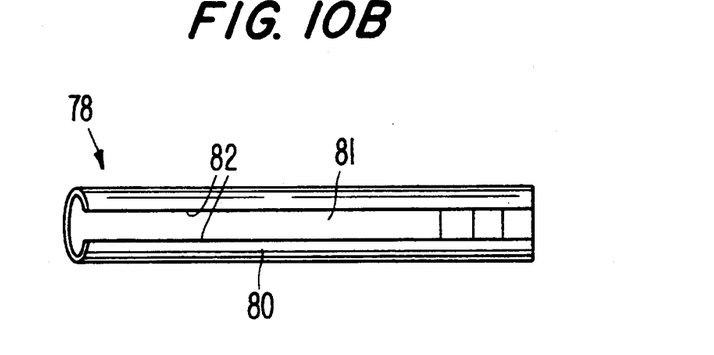

Reference is made to FIGS. 5-7 and 11 for illustrating the guide tube assembly 74 which, in the present embodiment, is situated within the irrigation tube 70. The guide tube assembly 74 includes the telescopic guide tube 32 which serves essentially to support the telescopic scope 20 and an elongated electrode guide tube 76 which is soldered beneath and along a length of the telescopic guide tube 32 to form an integral unit (FIG. 6). Included in the guide tube assembly 74 is an electrode guide ring 78 which is secured, as by spot welding, at its upper end to the inner periphery of the irrigation tube 70. It is also brazed to the guide tube 32 and soldered to the electrode guide tube 76. As seen in FIGS. 10a and 10b, the guide ring 78 defines a funnel like body 80 having a longitudinal space 81 between its longitudinal edges 82. The edges 82 are soldered against a distal end portion of the electrode guide tube 76. As seen in FIG. 7, the guide ring 78 blocks insertion of the electrode in the tube 70. Thus, when the scope 20 (not shown) is within tube 32 the only area open to insertion of the electrode is open tube 76. Because of the construction of the guide ring 78, improper insertion of the electrode into the irrigation tube is minimized since insertion of the electrode is blocked except for the tube 76. Hence, the electrode assembly can be easily inserted through the tube 76.

Figure 11:
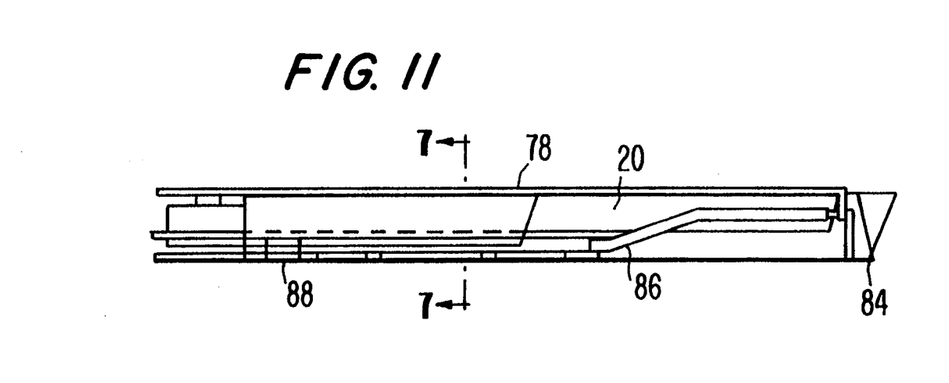
FIG. 11 is an enlarged and fragmented view, partly in section, illustrating the cooperation between the electrode assembly, telescopic assembly, and guide assembly of the present invention.
Figure 12:
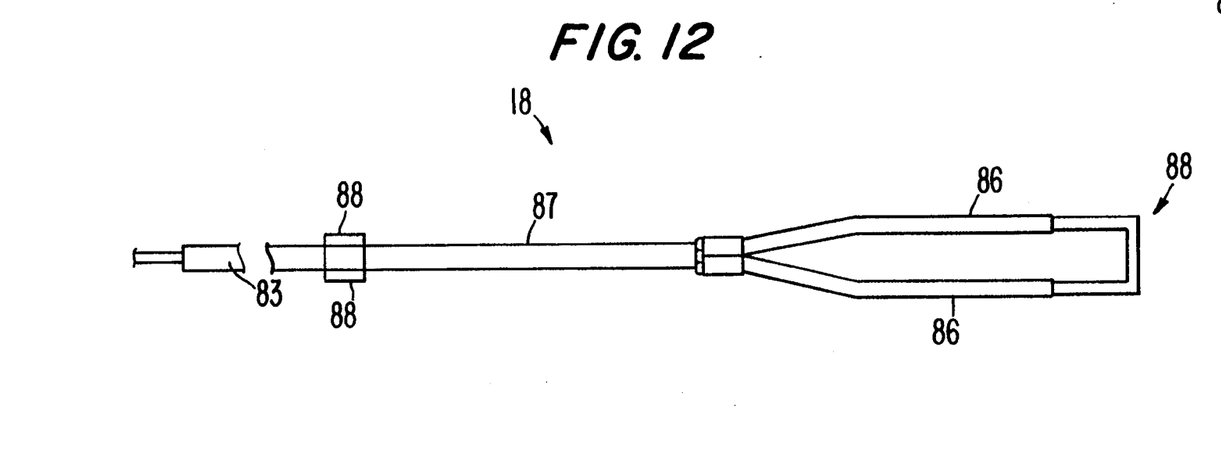
FIG. 12 is a plan view of one particular type of electrode assembly which is usable in conjunction with the present invention; and, FIG. 13 is an enlarged end view of the resecting electrode configuration.
Figure 13:
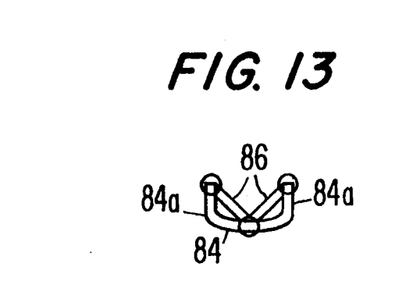

Reference is made to FIGS. 11-13 for illustrating the electrode assembly 18. The electrode assembly 18 has its proximal end portion 83 appropriately and removably attached to a source of High Frequency (H.F.) power connectable to the central block assembly 34, as will be described. The distal end of the electrode assembly 18 has a cutting loop 84 which extends from a pair of forked and insulated current carrying arms 86. The arms 86 are crimped and soldered together and define a shank portion 87 which is insertable through the electrode guide tube 76, as depicted in FIG. 6. The electrode assembly 18 can be of any known type suitable for use in a resectoscope. In this regard, the cutting loop 84, as depicted in FIG. 13, with a generally square side-shaped configuration. The parallel sides 84a have been determined to provide advantages in terms of resecting tissue, insofar as a procedurist is better able to view the depth of resection because of the parallel sides. The parallel sides 84c are interconnected by an integral radiused portion 84b. It will be appreciated that the electrode cutting loops can have other configurations. The electrode assembly 18 is provided with a one piece stability member 88 having a pair of wings 88a. The arcuate stability wings 88a serve as stabilizing means and also cooperate with the guide ring 78 and the irrigation tube 70 for insuring proper insertion of the electrode assembly 18 through the guide tube 76. Thus, the electrode stability wings 88a provide an anti-reversing function for further insuring proper installation of the electrode assembly into the guide tube 76.

Reference is now made back to FIGS. 1, 2, 8 and 9 for describing the electrode positioning assembly 16. In this particular embodiment, the central block assembly 34 is depicted as having a plurality of generally rectangular thumb engaging projections 90 which can be made of any suitable material. The projections 90 are spaced relative to one another and each is adapted to be engaged by a procedurist's thumb for allowing application of forces thereto so as to displace the same and displace the electrode assembly 18 such that the resection loop 84 extends from the outer sheath 50 for effecting resection. It will be appreciated that the procedurist's thumb is able to move freely from side projection to side projection and well as inferiorly of the central block assembly 34 to the depending projection 90. The projections 90 have slightly inclined radiused or flared edges 92 relative to a vertical plane so as to even better facilitate a user applying thumb pressure to the slidable central block assembly 34. Because of this construction the procedurist is better able to repeatedly and ergonomically force the electrode assembly 18 from the housing for purposes of effecting resection at the surgical site during an operation in a manner in which promotes surgical confidence regardless of prior type of resectoscope. Also, as earlier noted the procedurist's thumb need not be used for withdrawing the electrode.

The central block assembly 34 has an opening 96 adapted to removably receive the proximal end 83 of the electrode assembly 18. An electrode contact 98 has an opening 100 for reception of the electrode end and is therefore aligned with a passage (not shown) communicating with opening 96. The contact 98 is pivotally mounted by pin 102 to a High Frequency (HF) connector pin contact 104 that has a threaded opening 106 for connection to a High Frequency (HF) cable pin 108. A plug 110 covers the opening. A depressible push button 112 fits into an opening in the block 34 and is retained for limited sliding movement by retaining screw 114. A spring 116 mounted in the block tends to bias the contact 98 upwardly. When the electrodes' proximal end 83 is desired to be inserted, the push button 112 is depressed so that the opening 100 is in registry with opening 96. To latch the electrode assembly 18, the button 112 is released and the spring 116 drives the contact 98 upwardly against inner surfaces of the block 34, thereby retaining the electrode. Of course, the invention envisions other ways of releasably securing the electrode to a source of High Frequency power.

After having described the construction of the foregoing resectoscope it is believe that its operation is self-evident.

Certain changes may be made in the above described resectoscope assemblage without departing from the scope of the invention involved and it is intended that all matter contained in the description thereof or shown in the accompanying drawings shall be interpreted as illustrative and not in a limiting sense.

What is claimed is:

1. In an improved resectoscope including an outer sheath assembly insertable into a body at a surgical site, an electrode means displaceable within and relative to said outer assembly from a retracted, non-resecting position to an extended, resecting position and being energizable for resecting tissue at the surgical site; and electrode positioning means engageable by a procedurist's thumb for allowing transmission of applying forces thereto for overcoming a biasing force provided by a biasing means of said positioning means, said positioning means being displaced by the applying force to urge said electrode means to the resecting position at the surgical site and retracting said electrode means to said non-resecting position, the improvement comprising:

means coupled to said electrode positioning means for enabling a procedurist's thumb to engage said means at a plurality of positions for transmitting the applying forces thereto so as to overcome the biasing force and urge said electrode means to the resecting position, said thumb to engagable means being constructed to enable a procedurist's thumb to engage said thumb engageable means in a plurality of spaced positions which are peripherally located relative to said electrode positioning means; and, said biasing means of said electrode positioning means being operable to return said electrode means to the non-resecting position upon release of the applying forces thereto.

2. The resectoscope of claim 1 wherein said electrode positioning means includes a central block assembly coupled to a distal end portion of said electrode means and said thumb engageable means includes at least a projecting surface which is engageable by a procedurist's thumb in a plurality of positions generally circumferentially about an axis generally parallel to an axis of said outer assembly.

3. The resectoscope claim 1 wherein said electrode positioning means includes a central block assembly coupled to a distal end portion of said electrode means and said thumb engageable means includes a plurality of projections spaced from each other and extending generally laterally and inferiorly of said central block assembly.

4. In an improved resectoscope including an outer sheath assembly insertable into a body at a surgical site, an electrode means displaceable within and relative to said outer assembly from a retracted, non-resecting position to an extended, resecting position and being energizable for resecting tissue at the surgical site; and electrode positioning means engageable by a procedurist's thumb for allowing transmission of applying forces thereto for overcoming a biasing force provided by a biasing means of said positioning means, said positioning means being displaced by the applying force to urge said electrode means to the resecting position at the surgical site and retracting said electrode means to the non-resecting position, the improvement comprising:

means coupled to said electrode positioning means for enabling a procedurist's thumb to engage said means at a plurality of positions for transmitting the applying forces thereto so as to overcome the biasing force and urge said electrode means to the resecting position, said biasing means of said electrode positioning means being operable to return said electrode means to the non-resecting position upon release of the applying forces thereto; and an adjustable drip guard means for detachable retention on said outer assembly in any one of a plurality of selected positions so as to enable said drip guard means being positioned along the length of the outer assembly.

5. The resectoscope of claim 4 wherein said adjustable drip guard means includes a drip guard assembly coupled to an adjustable retaining member, said adjustable retaining member adapted to be mounted on a peripheral portion of said outer sheath assembly for selectively and firmly engaging therewith so as to be retained thereon in a preselected position.

6. In an improved resectoscope including an outer sheath assembly insertable into a body at a surgical site, an electrode means displaceable within and relative to said outer assembly form a retraced, non-resecting position to an extended, resecting position and being energizable for resecting tissue at the surgical site; and electrode positioning means engageable by a procedurist's thumb for allowing transmission of applying forces thereto for overcoming a biasing force provided by a biasing means of said positioning means, said positioning means being displaced by the applying force to urge said electrode means to the resecting position at the surgical site and retracting said electrode means to the non-resecting position, the improvement comprising:

means coupled to said electrode positioning means for enabling a procedurist's thumb to engage said means at a plurality of positions for transmitting the applying forces thereto so as to overcome the biasing force and urge said electrode means to the resecting position; and, said biasing means of said electrode positioning means being operable to return said electrode means to the non-resecting position upon release of the applying forces thereto; and said outer sheath assembly including an irrigation tube and telescopic guide tube means for supporting a telescope and connected thereto means for guiding and for stabilizing said electrode means for enabling easy insertion of said electrode means thereinto without disassembly of said resectoscope and for providing stabilized displacement of said electrode means relative to said outer assembly, said electrode guiding means including an electrode ring assembly fixedly connected to at least one of said telescopic guide tube means or said irrigation tube of said electrode outer sheath assembly, and said guide ring assembly being formed to define spaced edges which engage the periphery of said electrode guide assembly and block insertion of a proximal end of said electrode means into said guide ring assembly without disassembly of said resectoscope.

7. In an improved resectoscope including an outer sheath assembly insertable into a body at a surgical site, an electrode means displaceable within and relative to said outer assembly from a retracted, non-resecting position to an extended, resecting position and being energizable for resecting tissue at he surgical site; and electrode positioning means engageable by a procedurist's thumb for allowing application of forces thereto for overcoming a biasing force provided by a biasing means of said positioning means and said positioning means being displaced by the applying force to urge said electrode means to said resecting position a the surgical site and retracting said electrode means to said non-resecting position, the improvement comprising:

said outer sheath assembly including an irrigation tube and telescopic guide tube means for supporting a telescope and supported thereto means for guiding and stabilizing said electrode means for enabling easy insertion of said electrode means thereinto without disassembly of said resectoscope and for providing stabilized displacement of said electrode means relative to said outer assembly, said electrode guide means including and electrode guide ring assembly fixedly connected to at least one of said telescopic tube or said irrigation tube of said electrode outer sheath assembly and said guide ring assembly being formed to define spaced edges which engage the periphery of said electrode guide assembly and block insertion of a proximal end of said electrode means so as to facilitate insertion of said proximal end of said electrode means into said guide ring assembly without disassembly of said resectoscope.

* * * * *